United States Patent [19]

Rapoport et al.

[11] 4,110,329
[45] Aug. 29, 1978

[54] METALLIC DERIVATIVES OF NEOPINONE KETAL

[75] Inventors: Henry Rapoport; Randy B. Barber, both of Berkeley, Calif.

[73] Assignee: The Regents of the University of California, Berkeley, Calif.

[21] Appl. No.: 665,601

[22] Filed: Mar. 10, 1976

[51] Int. Cl.$^2$ .......................... C07F 15/00; C07F 3/14; C07F 5/00; C07D 489/02
[52] U.S. Cl. .................................. 260/270 A; 260/285
[58] Field of Search .................................. 260/270 A

[56] References Cited
PUBLICATIONS

J. Chatt, Chemical Reviews 48, p. 15 (1951).
Kabbe et al., Annalen der Chemie 656, 204–221.
Criegee et al., Angewadte Chemie 70, 173–179 (1958).
Becker et al., Organometalic Reactions vol. 3, pp. 326–327, 343, 354.
Siggia et al., Anal. Chem. 35, 1740–1743 (1963).
Streitwieser, Jr. et al., "Introduction to Organic Chemistry", 1976, p. 377.
March, "Advanced Organic Chemistry; Reactions, Mechanisms and Structure", 1968, pp. 306–307.
Sppenberger et al., Helv. Chim. Acta 51, 381–397 (1968).

*Primary Examiner*—Alton D. Rollins
*Assistant Examiner*—Mark L. Berch
*Attorney, Agent, or Firm*—R. J. Klostermann

[57] ABSTRACT

Certain mercury, lead, thallium, platinum or palladium derivatives of neopinone dimethyl ketal are provided which are useful as intermediates in the preparation of neopinone alkaloid, for example, 7-acetomercuri neopinone dimethyl ketal. Also provided are processes for preparing such derivatives and neopinone alkaloid.

9 Claims, No Drawings

METALLIC DERIVATIVES OF NEOPINONE KETAL

BACKGROUND OF THE INVENTION

1. Field of the Invention

This invention is directed to certain mercuric, lead, thallium, platinum and palladium derivatives of neopinone ketal and to a process for preparing them from thebaine or a salt of thebaine. It is also directed to processes for preparing neopinone alkaloid and mixtures containing neopinone and codeinone alkaloids utilizing such derivatives.

2. Description of the Prior Art

Neopinone or mixtures containing neopinone and codeinone can be converted into the antitussive dihydrocodeinone by well known means. They can also be converted to codeinone by the process described in our co-pending application entitled Process for Converting Neopinone to Codeinone, Ser. No. 665,602, filed on the same date herewith. Codeinone, of course, can be converted to codeine by the method of Gates et al.

Thebaine is the major alkaloid in papaver bracteatum; consequently, a process for converting thebaine into neopinone or mixtures containing neopinone and codeinone would be an advancement in the art.

SUMMARY OF THE INVENTION

This invention is directed to compounds represented by the following formula

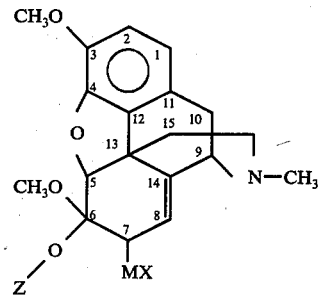

FORMULA I wherein M is mercuric, lead (IV), thallium (III) platinum (II) or palladium (II), X is an anion, and Z is lower alkyl, lower alkenyl, lower alkynyl, cycloalkyl, cycloalkenyl, monocarbocyclic aralkyl, or monocarbocyclic aralkenyl. The Roman numerals show the positive valence of the above-mentioned metals.

These compounds are useful as intermediates in the preparation of neopinone alkaloid and mixtures containing neopinone and codeinone alkaloids.

Another aspect of the invention is directed to a novel process for preparing the above-mentioned compounds which involves reacting thebaine or a salt of thebaine with suitable alcohols and a mercuric, lead (IV), thallium (III), platinum (II) or palladium (II) compound.

Another aspect of the invention is directed to a process for obtaining neopinone alkaloid or a mixture containing neopinone alkaloid and codeinone alkaloid which first involves reacting a compound represented by FORMULA I with an acid or a hydride reducing agent to cleave the carbon-metal bond of said compound and thereafter forming neopinone alkaloid or a mixture containing neopinone alkaloid and codeinone alkaloid.

Another aspect of the invention is directed to a process for producing neopinone dimethyl ketal and an acid salt of neopinone which comprises cleaving the carbon-metal bond of a compound represented by FORMULA I with an acid or a hydride reducing agent.

In the definitions of symbols in foregoing FORMULA I and where they appear elsewhere throughout this specification they have the following significance.

The term "lower alkyl" as used herein includes straight and branched chain radicals of up to 10 carbon atoms inclusive and is exemplified by methyl, ethyl, propyl, butyl, pentyl, octyl, nonyl and decyl. Preferred alkyl radicals contain 1 to 4 carbon atoms. The term "lower alkenyl" as used herein includes straight and branched chain radicals of up to 10 carbon atoms such as vinyl, allyl, methallyl, 4-pentenyl, 3-hexenyl, and 3-methyl-4-heptenyl. Preferred alkenyl radicals contain 2 to 4 carbon atoms. "Lower alkynyl" as used herein means straight and branched radicals of up to 10 carbon atoms such as ethynyl, propynyl, pentynyl and hexynyl. Preferred alkynyl radicals contain 2 to 4 carbon atoms. "Cycloalkyl" as used herein includes primarily cyclic alkyl radicals containing 5 to 7 carbon atoms inclusive such as cyclopentyl, cyclohexyl and cycloheptyl. The term "cycloalkenyl" as used herein includes primarily cyclic alkenyl radicals containing 5 to 7 carbon atoms inclusive such as 2-cyclohexenyl, and 2-cyclopentenyl. The term "aralkyl" as used herein includes lower alkyl substituted mono-carbocyclic aryl groups such as benzyl, phenylethyl, methylbenzyl, phenylpropyl and the like. Included in the term "aralkenyl" are lower alkenyl substituted monocarbocyclic aryl groups such as phenylally, phenylpentenyl, phenylbutenyl and the like. By "monocarbocyclic aryl" is meant an aryl radical of the benzene series, having six ring carbon atoms, and this term includes the unsubstituted phenyl radical and phenyl radicals substituted by any radical or radicals which are not reactive or would otherwise interfere with the formation of the desired compound under reaction conditions, such as nitro, lower-alkoxy, lower-alkylmercapto, lower-alkyl, halo, and the like. The substituted-phenyl radicals have preferably no more than one to three substitutents such as those given above, and furthermore, these substituents can be in various available positions of the phenyl nucleus and, where more than one substituent is present, can be the same or different and can be in various position combinations relative to each other. The lower-alkyl, lower alkoxy, and lower-alkylmercapto substituents each have preferably from one to three carbon atoms which can be arranged as straight or branched chains. The radical Z in the above FORMULA I, as stated in the foregoing, are inclusive of such groups as lower-alkyl, lower-alkenyl, cycloalkyl, cycloalkenyl, monocarbocyclic aralkenyl and monocarbocyclic aralkyl, and are preferably although not necessarily radicals of a solely hydrocarbon nature.

X may be any suitable anion, i.e., any anion derived from a mercuric, thallium (III), lead (IV), platinum (II) or palladium (II) compound which yields a measurable amount (about 1%) of the desired compound represented by FORMULA I by reacting with thebaine or a salt of thebaine under the reaction conditions described herein.

Such anions include acetate, acetyllide, benzoate, bromate, bromide, carbonate, chlorate, chloride, chromate, cyanide, fluoride, fluorsilicate, iodate, iodide, nitrate, oxalate, oxide sulfate, sulfide, thiocynate and perchlorate with acetate trichloroacetate, trifluoroacetate, hydroxide, bromide and chloride being preferred.

Representative compounds represented by FORMULA I include
7-acetomercurineopinone dimethyl ketal
7-acetolead (IV) neopinone dimethyl ketal, and
7-acetothallium (III) neopinone dimethyl ketal.

As mentioned the novel compounds of this invention are useful as intermediates in the preparation of neopinone alkaloid or a mixture containing neopinone alkaloid and codeinone alkaloid.

Compounds represented by FORMULA I can be prepared by one of the novel processes of this invention which involves reacting thebaine or a salt of thebaine, a suitable alcohol and a compound represented by the formula MX where M and X have the same significance as set out above.

Surprisingly, by following this process essentially quantitative yields of mercuric, lead (IV) or thallium (III) derivatives of neopinone ketal are obtained. As is known, there are a number of reactive sights on the thebaine molecule that the alcohol residue and the metallic compound could adduct to. Therefore, it was quite unexpected that the alcohol residue adds on in the 6-position and the metallic compound in the 7-position.

Suitable alcohols that may be used in this process include aliphatic, cycloaliphatic and araliphatic alcohols. Representative aliphatic alcohols contain from 1 to 10 carbon atoms, such as methanol, ethanol, propanol, decanol, allyl alcohol and vinyl alcohol. Because of their low cost and ready availability aliphatic alcohols having 1 to 4 carbon atoms are peferred.

Illustrative cycloaliphatic alcohols include those containing 5 to 7 carbon atoms such as cyclopentanol and cyclohexanol. Representative araliphatic alcohols include containing 1 to 10 carbon atoms in the aliphatic chain such as benzyl alcohol or phenylethyl alcohol.

Any mercuric, lead (IV), thallium (III), platinum (II) or palladium (II) compound that is reactive may be used in the process of this invention. By reactive is meant any mercuric, lead (IV), thallium (III), platinum (II) or palladium (II) compound which yields a measurable amount (about 1%) of the desired compound represented by FORMULA I on reaction with thebaine or a salt of thebaine under the reaction conditions described herein. Included are those compounds having any one of the previously mentioned anions. Specific examples include mercuric acetate, mercuric hydroxide, mercuric chloride, mercuric sulfate, thallium (III) triacetate, thallium (III) chloride, thallium (III) hydroxide, lead (IV) sulfate, lead (IV) acetate, lead (IV) chloride, platinum (II) chloride, platinum (II) hydroxide, palladium (II) chloride and palladium (II) bromide. Mercuric acetate because of its ready availability is preferred.

Typically the amount of mercuric, lead (IV), thallium (III), platinum (II) or palladium (II) compound per mole of thebaine or if a salt of thebaine per mole of thebaine in said salt, employed in the practice of this invention includes an amount from about 0.5 mole to about 3 moles, preferably from about 1.0 moles to about 2.0 moles. The amount of alcohol utilized to form the desired product of this invention may vary over a wide range. Typically, such amounts are in the range of from about 5 moles to 500 moles per mole of thebaine or if a salt of thebaine per mole of the thebaine in said salt.

In performing the process of this invention a suitable solvent is typically employed. Suitable solvents include tetrahydrofuran, tetrahydropyran, dichloroethane, methylene chloride, chloroform and others which will be apparent to the skilled worker. In the reaction it is preferred to employ an alcohol both as a reactant and as the solvent and when so doing excess amounts of alcohol are employed. However, when a solvent other than the reactant alcohol is employed the amount of alcohol is preferably in the range of from about 1 mole to 100 moles per mole of thebaine. In any event the amount of alcohol must be sufficient to permit formation of the desired product, and in most cases should not be less than 5 moles. Any suitable pressure from about 0.5 to 10 atmospheres may be used. The time required for a satisfactory degree of reaction may vary considerably according to the operating conditions. Because of this a few minutes to a few hours, specifically 5 minutes to 24 hours may be required for a satisfactory degree of reaction. In any specific case it is easy to determine the best time by a few preliminary experiments.

The novel compounds of this invention can be easily recovered by conventional means. For example, 7-acetomercurineopinone dimethyl ketal may be obtained by evaporating the filtrate of the reaction mixture.

According to another embodiment of this invention a compound represented by FORMULA I is reacted with an acid or a hydride reducing agent to thereby cleave the carbon-metal bond of said compound.

Useful acids, i.e., any compound that in solution will release a proton, include any strong or weak inorganic or organic acid. Suitable inorganic acids include halogen containing acids as hydrochloric, hydrofluoric or hydrobromic; phosphorus containing acids such as phosphoric, phosphorus, or hypophosphorus; sulfur containing acids such as sulfuric, hyposulfurous, or thiosulfuric; and others such as nitric, or manganic. Suitable organic acids include formic, acetic, chloroacetic and the like. It is preferred to use acetic or formic. Aqueous acid solutions are preferably utilized in the practice of this invention. Typically, the normality of these solutions is from about 0.1 to 10 with 1 to 3 being preferred. The acid is used in sufficient quantities to cleave the carbon metal bond. Frequently, this is an amount which is in excess of the stoichiometric amount required, preferably from about 10:1 to about 1000:1. The reaction proceeds at a temperature from about $-20°$ to about $100°$ C. For convenience, a preferred range in practice is from about $0°$ to $30°$ C. The reaction can be conducted in an inert solvent such as water, methanol, ethanol, propanol or aqueous mixtures of lower aliphatic alcohols. The solvent may be used in quantities suitable for dissolving the reactants, for instance, in a weight ratio of solvent to a compound represented by FORMULA I of about 1:1 to 500:1 or more. The time required for a satisfactory degree of reaction may vary considerably according to the reaction conditions. Because of this a few minutes to a few hours, specifically 10 minutes to 24 hours may be required for a satisfactory degree of reaction. In any specific case it is easy to determine the best time by a few preliminary experiments.

Alternatively, a compound represented by FORMULA I can be reacted with a hydride reducing agent to thereby cleave the carbon metal bond of FORMULA I. The reducing agents that may be used include the alkali metal borohydrides, the alkali metal aluminum hydrides and substituted alkali metal borohydrides and alkali metal aluminum hydrides wherein up to 3 hydrogen atoms are replaced with atoms or radicals which are relatively inert and non-reactive with respect to the reducing action characteristic of the hydrogen atoms of these compounds. Typical examples include sodium borohydride, lithium borohydride, sodium triethylborohydride, sodium trimethoxy-borohydride, triphenylborohydride, potassium borohydride, lithium aluminum hydride sodium aluminum dimethoxy hydride, and sodium aluminum disobutyl hydride. The hydride reducing agent is conveniently used in a sufficient amount to cleave the carbon-metal bond. Frequently this is an amount which is in excess of the stoichiometric amount required, preferably from about 2:1 to about 20:1. The reaction proceeds at a temperature from about $-20°$ to about 50° C. For convenience, a preferred range is from about 10° to about 30° C. Typically the reaction is conducted in an inert solvent such as water, methanol, ethanol, propanol or aqueous mixtures of lower aliphatic alcohols. The solvent may be used in quantities suitable for dissolving the reactants, for instance, in a weight ratio of solvent to a compound represented by FORMULA I of about 1:1 to 500:1 or more. The reaction may proceed rapidly, and frequently the duration of the reaction is about 0.1 to 20 hours. In any specific case it is easy to determine the best time by a few preliminary experiments.

As mentioned when an acid is utilized in the practice of this invention the carbon-metal bond is cleaved by hydrolysis and the neopinone acid salt thus formed is then treated with a basic agent to convert it into the alkaloid.

Although it is preferred to treat the neopinone acid salt with a basic agent in an aqueous medium, this does not exclude treatment in an anhydrous medium. The basic agent may be a mild alkaline agent such as sodium bicarbonate, alkali metal hydroxides, ammonia alkaline earth metal hydroxides, and the corresponding carbonates, bicarbonates, salts having an alkaline action such as sodium acetate, trisodium phosphate, and organic bases such as dimethyl amine or triethyl amine.

A sufficient amount of the basic agent is employed to neutralize the neopinone acid salt and thus liberate neopinone or a mixture of neopinone and codeinone. Generally the amount of basic agent utilized is such that the pH of the final medium containing neopinone or both neopinone and codeinone is from about 8 to about 13 at the treatment temperature.

Generally this treatment is carried out at a temperature of from about $-10°$ to about 50° C. It is preferred that the temperature be from about 0° to about 20° C. By keeping the temperature around 0° C. the basic treatment results in essentially all neopinone alkaloid. At higher temperature a mixture containing neopinone alkaloid and codeinone alkaloid results in a ratio of codeinone:neopinone of about 3:1 to 1:4.

Isolation of the neopinone alkaloid or the mixture containing neopinone alkaloid and codeinone alkaloid does not present any special difficulty. They may be recrystallized if necessary from a suitable solvent or extracted with a water immiscible solvent such as chloroform, washing with water and then drying and evaporating the solvent.

When the metal to carbon bond is cleaved with the hydride reducing agent according to the practice of this invention the resulting neopinone ketal may be hydrolized to the corresponding neopinone alkaloid or a mixture containing neopinone and codeinone by a known procedure which involves using an aqueous acid and thereafter treating with a basic agent. Such a hydrolysis procedure is known and described in a publication by W. F. Fleischhacker and H. Markut, *Monatshefte für Chemie*, 102, 569–586 (1971) which is incorporated herein by reference.

For example, neopinone dimethyl ketal is hydrolyzed for fifteen minutes at 40° C. with 6 normal hydrochloric acid. Alternatively, the same acids and conditions mentioned previously for cleaving the metal bond of FORMULA I may be used to hydrolyze the neopinone ketal. Likewise, the same basic agents and conditions mentioned previously to liberate neopinone or a mixture of neopinone and codeinone may be employed to liberate the alkaloids.

Neopinone or a mixture containing neopinone and codeinone can be converted into dihydrocodeinone by well known means. Dihydrocodeinone is useful as an antitussive.

The invention is illustrated by the following examples. All parts are by weight unless otherwise stated.

EXAMPLE 1

Preparation of 7-hydroxymercurineopinone Dimethyl Ketal

A solution of thebaine (311 mg.; 1.0 mmol) in methanol (10 ml.) was added to a suspension of mercuric acetate (478 mg.; 1.5 mmol) in methanol (10 ml.) at reflux under $N_2$ with magnetic stirring for 30 – 40 min. The hot mixture was filtered to remove a portion of the excess mercuric acetate, washed with a small amount of methanol, and then the solvent was removed in vacuo to a residue of 921 mg. This material was dissolved in $CHCl_3$, washed with sat. aq. $NaHCO_3$, water, dried over $Na_2SO_4$, filtered, and solvent removed in vacuo to give 325 mg. which by nmr analysis was a mixture of stereoisomers at the 7-position.

EXAMPLE 2

Preparation of 7-acetomercurineopinone Dimethyl Ketal

A solution of thebaine (1.00 g., 3.22 mmol) in methanol (40 ml.) was added to a stirred suspension of mercuric acetate (1.54 g., 4.82 mmol, 150 mol %) in methanol (30 ml.) at reflux for 50 min. under $N_2$. After reflux, the mixture was filtered and the solvent evaporated in vacuo to give a residue of 2.67 g.

EXAMPLE 3

Preparation of Neopinone from Thebaine

A solution of thebaine (1.00 g., 3.22 mmol) in methanol (40 ml.) was added to a stirred suspension of mercuric acetate (1.54 g., 4.82 mmol, 150 mol%) in methanol (30 ml.) at reflux for 50 min. under $N_2$. After reflux, the mixture was filtered and the solvent evaporated in vacuo to give 2.67 g. of residue. This residue was taken up in 100 ml. of 3N acetic acid (17 ml. glacial HOAc diluted to 100 ml. $H_2O$) and stirred at room temperature under $N_2$ for 100 min. at which time 70 ml. of sat. aq. KBr was added to ppt. $HgBr_2$. The precipitated mercury salts were filtered off through filter-aid after stirring for about 1 hour. The filtrate was cooled to 0° C. and 50 ml. of chloroform was added. The aqueous phase was basified to pH 12 with concentrated aq. NaOH. The chloroform layer was separated and the aqueous layer extracted with several portions of chloroform. All of the chloroform extracts were combined, washed with water, dried over $Na_2SO_4$, filtered and evaporated in vacuo to give crystalline neopinone; 0.995 g. (100%).

Subsequent reactions on a 1.0 g. scale gave yields consistently of 95 – 100%, and on a 3.0 g. scale gave 97% of clean neopinone; nmr δ 2.45 (s, 3H), NCH$_3$), 3.85 (s, 3H, ArO-OH$_3$), 4.95 (s, 1H, C-5, 5.50 (q, 1H, C-8), 6.65 (s, 2-H, C-1,2).

EXAMPLE 4

Preparation of Neopinone Dimethyl Ketal

A solution of thebaine (311 mg.; 1.0 mmol) in 10 ml. methanol was added to a mixture of mercuric acetate (637 mg.; 2.0 mmol) in 10 ml. of methanol at reflux under N$_2$ for 35 min. The reaction mixture was cooled to 0° C. and basified with 10 ml. of 3N NaOH and then treated with 10 ml. of 3N NaOH that was 0.5M in NaBH$_4$. Evaporation of the methanol in vacuo and then extraction of the aqueous phase with chloroform gave an oil of 382 mg. which was one peak by gc. and one spot by tlc. This material was preparative tlc'd on silica (CHCl$_3$-MeOH; 85:15) and Kugel Rohr distilled (90°/.1 mm. Hg) to give 214 mg. of neopinone dimethyl ketal as a clear colorless oil; nmr δ 2.50 (s, 3H, N-CH$_3$), 3.00

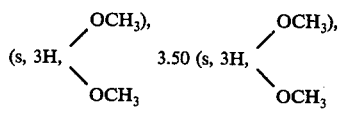

3.90 (s, 3H, Ar-OCH$_3$), 4.70 (s, 1H, C-5), 5.40 (q, 1H, C-8), 6.67 (q, 2H, C-1,2); $[\alpha]_D^{CHCl_3}$ —661.9°.

Anal. Calcd. for C$_{20}$H$_{25}$NO$_4$: C, 69.94; H, 7.35; N, 4.08. Found: C, 69.73; H, 7.16; N, 3.95.

As various changes could be made in the above methods and products without departing from the scope of the invention, it is intended that all matter contained in the above description shall be interpreted as illustrative. It is to be understood therefore that the invention is not limited as defined by the appended claims.

What is claimed is:

1. A compound represented by the following formula

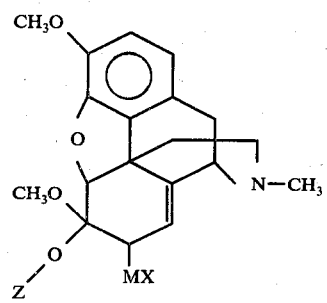

where M is mercuric, platinum (II) or palladium (II), X is a suitable anion, selected from the group consisting of acetate, acetyllide, benzoate, bromate, bromide, carbonate, chlorate, chloride, chromate, cyanide, fluoride, fluorosilicate, iodate, iodide, nitrate, oxalate, oxide, sulfate, sulfide, thiocyanate perchlorate hydroxide, trichloroacetate, and trifluoroacetate, Z is lower alkyl, cycloalkyl, or monocarbocyclic aralkyl.

2. A compound according to claim 1 wherein Z is an alkyl radical containing 1 to 4 carbon atoms, a cycloalkyl radical containing 5 to 7 carbon atoms or monocarbacyclic aralkyl radical containing 1 to 4 carbon atoms in the alkyl chain.

3. A compound according to claim 2 wherein M is mercuric.

4. A compound according to claim 3 wherein Z is alkyl.

5. A compound according to claim 4 wherein Z is methyl.

6. A compound according to claim 2 wherein X is hydroxide, acetate, bromide, chloride, trichloroacetate or trifluoroacetate.

7. A compound according to claim 3 wherein X is hydroxide, acetate, bromide, chloride, trichloroacetate or trifluoroacetate.

8. A compound according to claim 5 wherein X is hydroxide, acetate, bromide, chloride, trichloroacetate or trifluoroacetate.

9. A compound according to claim 8 where in X is acetate.

* * * * *